United States Patent [19]

Peterson et al.

[11] Patent Number: 4,859,388
[45] Date of Patent: Aug. 22, 1989

[54] IMPROVED METHOD OF MAKING DISCRETE AIRLAID ABSORBENT FIBROUS ARTICLES

[75] Inventors: David A. Peterson, Cincinnati, Ohio; Douglas H. Benson, West Harrison, Ind.

[73] Assignee: The Proctor & Gamble Company, Cincinnati, Ohio

[21] Appl. No.: 117,898

[22] Filed: Nov. 3, 1987

Related U.S. Application Data

[60] Division of Ser. No. 820,901, Jan. 16, 1986, abandoned, which is a continuation of Ser. No. 576,099, Feb. 1, 1984, abandoned.

[51] Int. Cl.$^4$ ............................................. B27N 3/14
[52] U.S. Cl. .................................... 264/121; 264/517; 264/118; 264/119
[58] Field of Search ............... 264/517, 518, 112, 121, 264/324, 119, 118; 425/83.1, 80.1

[56] References Cited

U.S. PATENT DOCUMENTS

| | | | |
|---|---|---|---|
| 2,073,329 | 3/1937 | Winter | 154/33 |
| 2,295,155 | 9/1942 | Brown et al. | 425/80.1 |
| 2,698,271 | 12/1954 | Clark | 264/121 |
| 2,940,135 | 6/1960 | Heritage | 264/518 |
| 3,070,838 | 1/1963 | Hostettler | 425/81.1 |
| 3,518,726 | 7/1970 | Banks | 19/144.5 |
| 3,857,657 | 12/1974 | Teed | 264/517 |
| 3,939,240 | 2/1976 | Savich | 264/517 |
| 4,005,957 | 2/1977 | Savich | 425/80 |
| 4,375,447 | 3/1983 | Chung | 264/518 |
| 4,469,656 | 9/1984 | Ishii | 264/518 |

Primary Examiner—Jan. H. Silbaugh
Assistant Examiner—Mary Lynn Fertig
Attorney, Agent, or Firm—John M. Pollaro; Thomas J. Slone; Fredrick H. Braun

[57] ABSTRACT

An improved, continuous airlaying apparatus for making airlaid articles such as discrete absorbent fibrous cores for catamenial napkins and disposable diapers and the like having high structural integrity, and good edge definition. The articles are airlaid in discrete cavities as they pass through a deposition zone of the apparatus, and are compacted a predetermined amount prior to their being removed from their respective deposition cavities. An exemplary mechanism for effecting the compacting comprises a lugged cylinder having circumferentially spaced lugs which are configured and pitched to mesh in a quasi gear-like manner with the deposition cavities.

1 Claim, 3 Drawing Sheets

IMPROVED METHOD OF MAKING DISCRETE AIRLAID ABSORBENT FIBROUS ARTICLES

This is a continuation of application Ser. No. 820,901 filed Jan. 16, 1986, now abandoned which is a continuation of application Ser. No. 576,099, filed Feb. 1, 1984, now abandoned.

TECHNICAL FIELD

This invention pertains to forming airlaid articles such as discrete absorbent cores the catamenial napkins or disposable diapers. More particularly it pertains to making such discrete articles so that they have high structural integrity, and good edge definition (i.e., the edge of the article being made in the image of the edge of the cavity). This also limits the degree of length/width growth of the articles if they are subjected to calendering after being removed from the cavities. This is, basically, achieved by compacting each airlaid mass prior to removing it from its formation cavity.

BACKGROUND ART

A drum-type airlaying apparatus for making discrete absorbent fibrous articles is disclosed, for example, in U.S. Pat. No. 2,073,329 which issued Mar. 9, 1937 to C. P. Winter, and which includes a broadly divergent duct which extends from his drylap disintegrator (i.e., means for air entraining fibers) to the periphery of his first deposition drum. Another drum-type airlaying apparatus for airlaying discrete absorbent fibrous articles which has a similarly broadly divergent duct for air-entrained fiber flow is disclosed in U.S. Pat. No. 4,005,957 which issued Feb. 1, 1977 to Peter P. Savich. A drum-type airlaying apparatus for making a concatinated stream of absorbent fibrous articles is disclosed in U.S. Pat. No. 3,518,726 which issued July 7, 1970 to C. T. Banks. A belt-type airlaying apparatus having a duct for air-entrained fibers which is sharply angled obliquely downstream with respect to the laydown belt is disclosed in U.S Pat. No. 4,375,447 which issued Mar. 1, 1983 to Raymond Chung.

DISCLOSURE OF THE INVENTION

In accordance with one aspect of the invention, an improved airlaying apparatus for making discrete absorbent fibrous articles is disclosed. The apparatus is of the type which includes a deposition chamber; an endless deposition member having a plurality of article formation cavities disposed in machine direction spaced relation thereon, and wherein each of the cavities has a foraminous bottom wall; means for directing air-entrained fibers towards a machine-direction span of said deposition member; and means for vacuum exhausting the fiber-entrainment air from the apparatus. The improvement provides means for compacting each discrete absorbent fibrous article prior to its being removed from its respective formation cavity. An exemplary deposition member comprises a deposition drum having the deposition cavities disposed in circumferential relation about the periphery of the drum; and an exemplary compacting means comprises a lugged cylinder having circumferentially spaced lugs which are configured and pitched to mesh with the discrete formation cavities in a quasi gear-like manner. That is, the cylinder rotates in timed relation with the passing cavities; and a lug enters each cavity in a rolling motion to effect a predetermined degree of compaction.

BRIEF DESCRIPTION OF THE DRAWINGS

While the specification concludes with claims which particularly point out and distinctly claim the subject matter regarded as forming the present invention, it is believed the invention will be better understood from the following descriptions taken in conjunction with the accompanying drawings in which identical features in the several views are identically designated and in which:

DETAILED DESCRIPTION OF THE INVENTION

Figure 1:
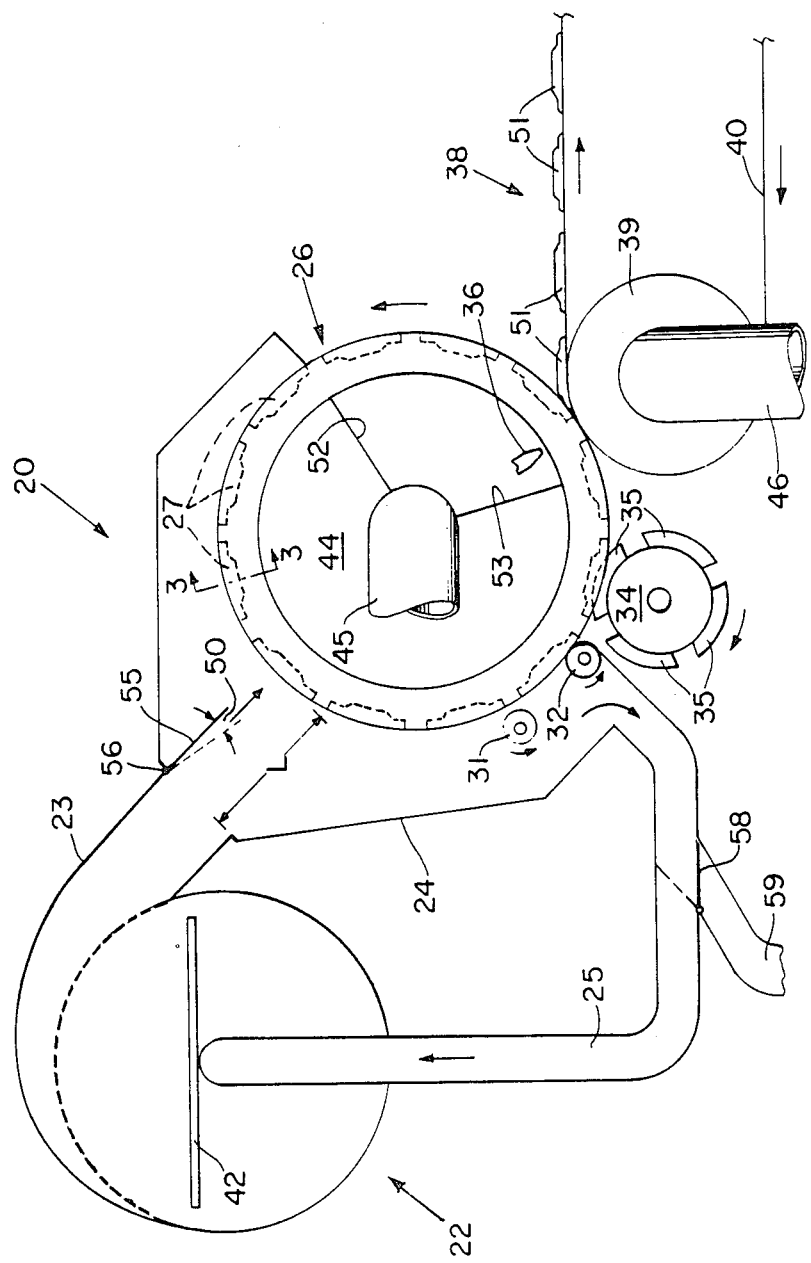
FIG. 1 is a somewhat schematic, fragmentary side elevational view of an apparatus embodiment of the present invention.

A fragmentary portion of an exemplary drum-type apparatus for making discrete absorbent fibrous articles such as cores of catamenial napkins or disposable diapers in accordance with the present invention is designated 20 in FIG. 1. As further shown in FIG. 1, apparatus 20 comprises a disc-type hammermill 22 having a columnar discharge chute 23, a hood 24, a recirculation manifold 25, a deposition drum 26 having a plurality of deposition cavities 27 disposed in circumferentially spaced relation about its periphery, two scarfing rolls 31 and 32, a lugged cylinder 34 having a plurality of radially extending lugs 35, a blow-off means or nozzle 38, and a take-away conveyor 38 comprising a vacuum-type return roll 39 and a foraminous endless belt 40. Means not shown are provided for feeding a drylap web into infeed slot 42 of hammermill 22 at a predetermined rate; means for powering and controlling hammermill 22; means for rotating drum 26, scarfing rolls 31 and 32, and conveyor 38 in timed relation; means for maintaining a predetermined degree of vacuum in vacuum manifold 44 of drum 26 via vacuum duct 45, and means for maintaining a predetermined level of vacuum inside a sector of return roll 39 through vacuum duct 46. Additionally, a somewhat columnar stream 50 of air-entrained fibers is shown in FIG. 1 to be exiting from the discharge chute 23 of hammermill 22 and directed generally radially towards a sector of drum 26 having a relatively small circumferential length; and an endless stream of discrete absorbent fibrous articles 51 is shown moving rightwardly on belt 40 of take-away conveyor 38. As used herein, a drylap web is a web of fibers which are subject to being disassociated and air-entrained by the action, for example, of hammermill 22.

Briefly, apparatus 20 comprises means for converting an endless length or roll of drylap web into a stream of discrete absorbent fibrous articles having good edge definition and structural integrity. The hammermill—alternately designated a fiberizer or disintegrator—disassociates the fibers of the drylap web and then discharges a relatively high velocity stream of air-entrained fibers which stream is directed generally radially towards a relatively short circumferential span of the periphery of drum 26. The velocity and mass derived momentum of the fibers in the stream injects them into a deposition cavity disposed on the periphery of the drum while the substantially smaller momentum of the fiber-entrainment air enables the bulk of the fiber-entrainment air to turn upstream with respect to the periphery of the drum and be drawn through the foraminous bottom walls of substantially empty additional deposition cavities by the vacuum maintained in vacuum manifold 44 of drum 26. Indeed, as is more fully described heeinafter, each deposition cavity is preferably overfilled in its entirety (i.e., its full width and circumferential length), and the excess is scarfed away by scarfing rolls 31 and 32. Then, the mass of fibers disposed in each filled deposition cavity is compacted a predetermined amount by the action of a lug 35 on the lugged cylinder 34 to complete the formation of a discrete airlaid article 51 having good edge definition and structural integrity as a result of being compacted before being removed from its deposition cavity. The discrete articles are then transferred to the take-away conveyor by the joint action of the blow-off nozzle 36, and vacuum in a facing sector of the conveyor return roll 39. Parenthetically, the bulk of the fiber-entrainment air exits via substantially empty deposition cavities because of the flow impeding effect of the fiber build up in the deposition cavity passing under the stream 50 of air-entrained fibers.

Figure 2:
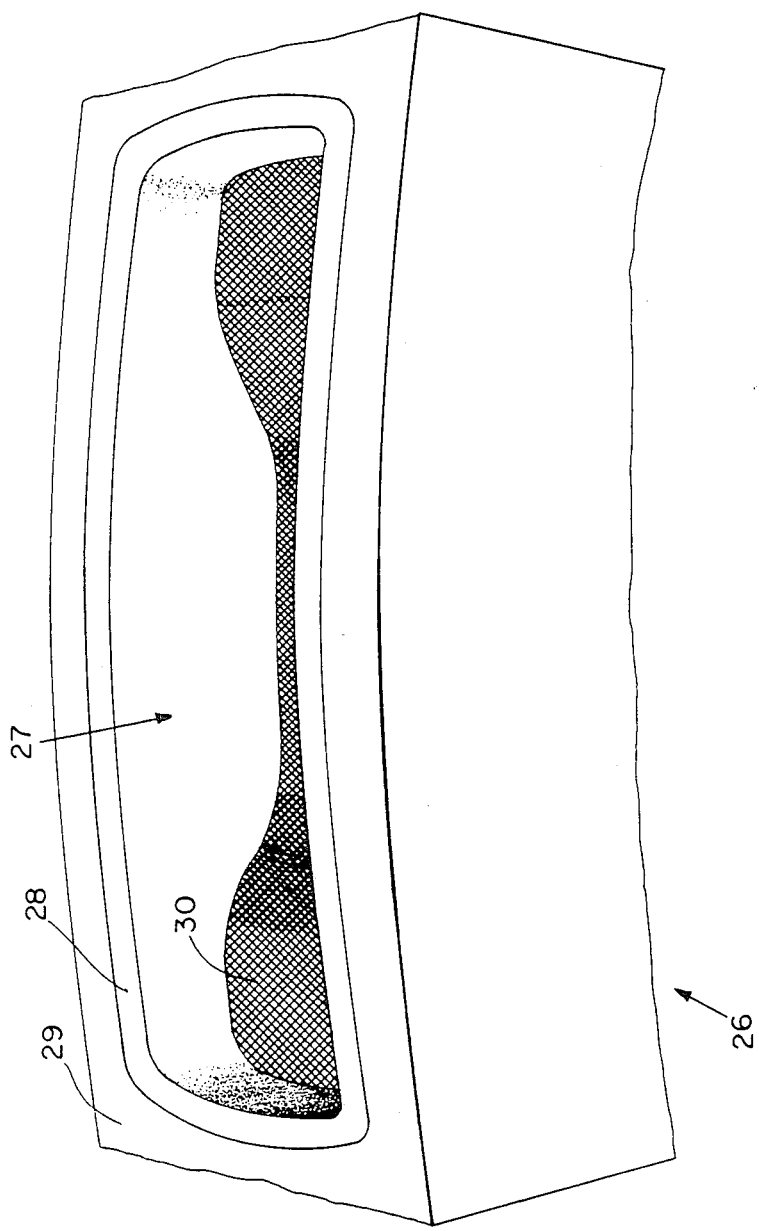
FIG. 2 is an enlarged scale, fragmentary perspective view of a deposition cavity disposed on the periphery of the deposition drum of the apparatus shown in FIG. 1.

A deposition cavity 27 is shown in a perspective view, FIG. 2, of a fragmentary portion of the periphery of deposition drum 26. The deposition cavity has a stepped configuration to provide articles 51 having substantially less basis weight (i.e., weight of fibers per unit of its plan-view area) in their end regions than their center spans. That is, as the articles 51 are formed they have generally uniform density, thick center spans and relatively thin end regions due to the geometry of the deposition cavities 27. Then, through the action of the lugged cylinder 34, the articles are compacted to achieve improved structural integrity; to have their edges more clearly defined; and to limit their length/width growth in the event they are further calendered or compacted after being removed from the deposition cavities. Additionally, the discrete articles 51 are preferably calendered and enveloped in suitable covering materials and such other converting operations as desired are effected downstream from the deposition member to produce finished disposable consumer products comprising airlaid fibrous cores; for example, catemenial napkins and/or disposable diapers.

Figure 3:
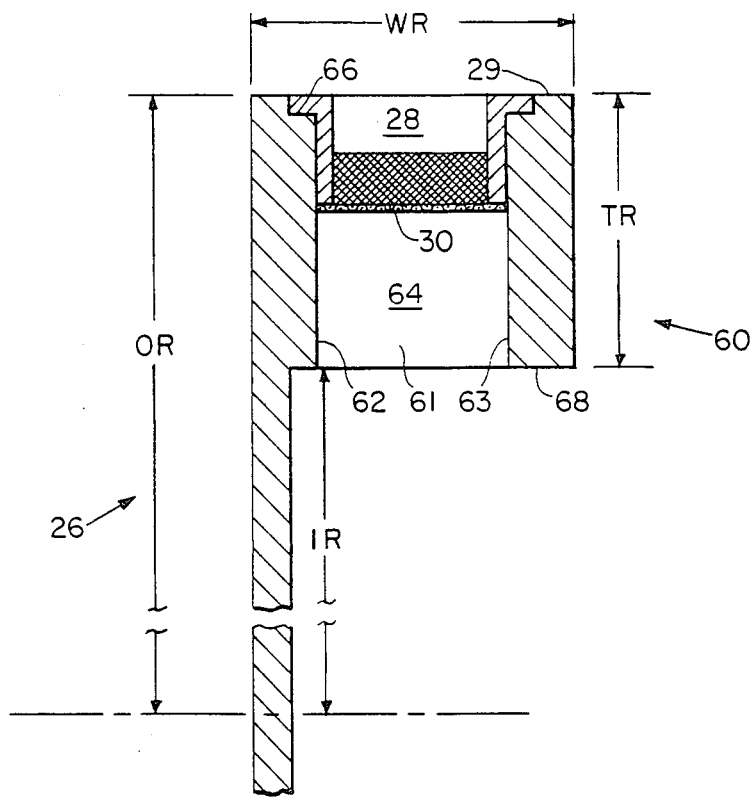
FIG. 3 is an enlarged scale, fragmentary sectional view taken along section line 3—3 of FIG. 1 which section line extends radially through the center of a deposition cavity disposed in the rim of the deposition drum of the apparatus shown in FIG. 1.

Referring now to FIG. 3, a transverse-radial section of drum 26 is shown to have an outer radius OR and inner radius IR; a rim 60 having a radial thickness TR and a transverse width WR. The rim 60 as shown in FIG. 3 has a radially extending hole 61 machined through it which hole, as shown is defined by side walls 62 and 63, and end walls 64, only one of the end walls being visible in the sectional view. Of course, hole 61 is only one of a plurality of such holes which are disposed in the rim of drum 26; one for each deposition cavity 27, FIG. 1, which in the exemplary apparatus 20 number twelve which are spaced at thirty degrees center-to-center. The radially outwardly facing surface of the rim has a recess 66 machined in it to accommodate the flange of a deposition cavity insert 28 so that the radially outwardly facing surface of the insert is flush with the radially outwardly facing surface of the rim, and so that together they constitute the periphery 29 of the drum. A piece of screen or otherwise foraminous material is secured to the bottom end of insert 28 to constitute its bottom wall 30. The surface of the drum having a radius IR is designated sealing surface 68. The vacuum manifold 44, FIG. 1, which is stationary (i.e., does not rotate with drum 26) is provided with sealing means which coacts with sealing surface 68, FIG. 3, to enable the vacuum applied to the manifold to draw fiber-entrainment air downwardly through the cavities 27 and holes 61 which pass over the vacuum manifold as the drum rotates.

Referring again to FIG. 1, apparatus 20 is shown to further comprises an optional baffle plate 55 which is pivotally mounted on the upstream lip of chute 23 by pivot pin 56; a recirculation dump valve 58; and a recirculation dump duct 59. The angular position of baffle plate 55 can be adjusted to precipitate a downstream velocity vector component to the stream 50 of fibers to match the peripheral velocity of drum 26, or to otherwise provide a sufficient downstream velocity vector component of stream 50 to achieve even filling of the deposition cavities 27. The recirculation dump valve 58, and the recirculation dump duct 59 are provided to divert air-entrained fibers from the recirculation manifold 25 when apparatus 20 is turned off to prevent fibers in the recirculation manifold from precipitating deliterious ramifications during start-ups of apparatus 20.

EXEMPLARY EMBODIMENT OF APPARATUS 20

An exemplary apparatus of the configuration shown in FIG. 1 was sized and configured to make twelve articles 51 per revolution of the drum. In this apparatus, the articles are formed in deposition cavities having lengths of six-and-six-tenths inches (about 17.8 cm.) and which cavities are spaced eight-and-one-half inches (about 21.6 cm.) center-to-center about the periphery of the drum. The cavities are configured to be seven-tenths of an inch deep (about 1.8 cm) in their and regions, and one-and-three-tenths inches deep (about 3.3 cm) in their center spans in order to make articles 51 having nominal fiber weights of about eight grams each. The hood wraps the drum approximately one-hundred-eighty degrees, centered about the upstream wall of the discharge chute 23 as indicated in FIG. 1. The vacuum manifold 44 spans about two-hundred-sixty degrees of the drum, and is so disposed that its upstream end 52 is subjacent the upstream end of the hood, and so that its downstream end 53 is positioned just upstream of the return roll 39 and nozzle 36. The lugged cylinder 34 is configured generally as shown with four lugs 35. The lugs are disposed on the same pitch as the pitch of the deposition cavities on drum 26 so that cylinder 34 and the drum mesh (albeit preferably not in contacting relation) in a gear-like manner as they are rotated in synchronus relation. The disk hammermill 22 was obtained from Curt G. Joa, Inc., and is their hammermill model number 85R-9505-B. This hammermill acts somewhat like a quasi centrifugal air blower inasmuch as it draws air into its intake. Thus, by connecting the recirculation manifold 25 to the intake of the hammermill, no other means need be provided to effect flow in the recirculaton manifold.

Apparatus 20 is preferably operated with the stream 50 having a length L of up to about fourteen inches (about 35.6 cm.), and more preferably from about ten to about twelve inches (about 25.4 to about 30.5 cm.); a velocity of stream 50 of from about two-thousand to about fifteen-thousand feet per minute (about 0.61 to about 4.57 Km. per minute), and more preferably from about six-thousand to about ten-thousand feet per minute (about 1.83 to about 3.05 Km. per minute); a flow rate of stream 50 of from about one-thousand to about fifteen-hundred cubic feet per minute (about 28.3 to about 42.5 cubic meters per minute); a fiber to air weight ratio in stream 50 of from about six-to-one to about thirty-to-one, and more preferably from about seven-to-one to about sixteen-to-one; and a peripheral velocity of drum 26 preferably from about two-hundred-fifty to about seven-hundred feet per minute (about 76.2 to about 213 meters per minute).

The drylap used in the exemplary apparatus described above was obtained from The Buckeye Cellulose Corporation and comprised from about seventy-five to about one-hundred percent native softwood fibers, and from about zero to about twenty-five percent hardwood fibers.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An improved method of making discrete absorbent fibrous articles by depositing air-entrained fibers in discrete closed-bottom deposition cavities, said improvement comprising the steps of:

rotating a drum having said cavities:

overfilling each of said cavities with said fibers;

continuously scarfing away the excess of said fibers to thereby form in each said cavity an uncompacted preform of a said article having the size and shape of said cavity, a thickness equal to the depth of said cavity, and an outwardly exposed top surface;

rotating a lugged cylinder in synchronous relation with said drum;

mechanically compacting each said preform to reduce its thickness by a predetermined amount while it is disposed in its respective said rotating cavity, said compacting being effected by mechanical rolling of a lug of said lugged cylinder against said top surface and thereby converting each said preform into a said article; and then discharging each said article from its respective deposition cavity.

* * * * *

UNITED STATES PATENT AND TRADEMARK OFFICE
CERTIFICATE OF CORRECTION

PATENT NO.   :   4,859,388

DATED        :   August 22, 1989

INVENTOR(S)  :   David A. Peterson, Douglas H. Benson

It is certified that error appears in the above-identified patent and that said Letters Patent is hereby corrected as shown below:

Title page:

Assignee: delete "Proctor" and insert therefor --Procter--.

Column 2, line 36, delete "38" and insert therefor --36--.

Column 3, line 9, delete "heeinafter" and insert therefor --hereinafter--.

Column 3, line 48, delete "catemenial" and insert therefor --catamenial--.

Column 4, line 2, delete "," (comma) and insert therefor --.-- (period).

Column 4, lines 24 - 25, delete "deliterious" and insert therefor --deleterious--.

Column 4, line 37, delete "and" and insert therefor --end--.

Column 6, line 8, delete ":" (colon) and insert therefor --;-- (semicolon).

UNITED STATES PATENT AND TRADEMARK OFFICE
CERTIFICATE OF CORRECTION

PATENT NO. : 4,859,388

DATED : August 22, 1989

INVENTOR(S) : David A. Peterson, Douglas H. Benson

It is certified that error appears in the above-identified patent and that said Letters Patent is hereby corrected as shown below:

Column 6, line 23, after "then" delete --discharging--.

Column 6, line 24, before "each" insert --discharging--.

Signed and Sealed this

Second Day of October, 1990

Attest:

HARRY F. MANBECK, JR.

*Attesting Officer*     *Commissioner of Patents and Trademarks*